United States Patent [19]

Aldinger

[11] Patent Number: 4,695,283
[45] Date of Patent: Sep. 22, 1987

[54] ENDOPROSTHESIS

[76] Inventor: Günther Aldinger, Engelfriedshalde 13, 7400 Tuebingen, Fed. Rep. of Germany

[21] Appl. No.: 749,880

[22] Filed: Jun. 27, 1985

Related U.S. Application Data

[62] Division of Ser. No. 484,143, Apr. 8, 1983, abandoned.

[30] Foreign Application Priority Data

Apr. 10, 1982 [DE] Fed. Rep. of Germany ....... 3213437

[51] Int. Cl.⁴ ............................................... A61F 2/30
[52] U.S. Cl. ....................................... 623/23; 623/16
[58] Field of Search .................... 623/18, 19, 20, 21, 623/22, 23; 128/92 C, 92 CA; 403/173, 174

[56] References Cited

U.S. PATENT DOCUMENTS

| 3,894,297 | 7/1975 | Mittelmeier | 623/22 |
| 4,064,568 | 12/1977 | Grundei et al. | 623/20 |
| 4,068,324 | 1/1978 | Townley et al. | 623/23 |
| 4,185,383 | 1/1980 | Heimke et al. | 433/173 |
| 4,292,695 | 10/1981 | Koeneman | 623/18 |

OTHER PUBLICATIONS

"Individually Shaped Cementless Hip Endoprosthesis" by G. Aldinger.

Primary Examiner—Richard J. Apley
Assistant Examiner—David J. Isabella
Attorney, Agent, or Firm—Michael J. Striker

[57] ABSTRACT

An endoprosthesis insertable in a bone cavity comprises an anchoring shaft having circular steps at least in supporting regions (X,Y) of the anchoring shaft in which a support of said anchoring shaft in the bone takes place. The shaft has at a free end remote from a mouth of the bone opening a straight portion. The steps are formed in at least the straight portion one after another without undercuts. The shaft conically widens from said end towards an end opposite to said free end. The steps have contours which are at least in the region in which the steps are supported in the bone, individually adjusted to respective cross-sections of the bone hollow, which cross-sections exist at the positions of the individual steps when the endoprosthesis is inserted into the bone.

8 Claims, 14 Drawing Figures

ENDOPROSTHESIS

This is a division of application Ser. No. 484,143, filed Apr. 8, 1983, now abandoned.

BACKGROUND OF THE INVENTION

The invention relates to an endorothesis including an anchoring element.

Anchoring of protheses, and particularly of endoprotheses in a human bone has been a major problem in the prior art. This problem occurred with total protheses (for example, hip- head-neck-resection) and for joint-surface-substitute endoprotheses (for example, hip, head cap-knee slots-endoprotheses) and also for combinations of protheses (for example, upper shank part of the knee total endoprothesis).

The protheses which substitute for natural body parts—vary in sizes, shapes, structures, angular positions, lengths, widths as compared to a relatively small number of filling protheses or endoprotheses, support or volume substituting parts of various materials. This means that a surgeon is in many instances, forced to adjust the bone of a patient to a prothesis model for anchoring the prothesis in the bone. In many cases this means that a bone substance should be removed for adjusting or fitting in the filling prothesis; under both conditions pressure, pulling and torsion forces which can occur on the prothesis insert or on the attachment place must be considered in the bone structure to be adjusted.

With conventional shaft-like implanted endoprotheses (for example hip endoprotheses) a relatively thin prothesis part must be anchored in a wider bone shaft. If there is spongiosa in the bone its balk or mesh structure is disturbed and its initial supporting function can not be carried out.

With conventional cement anchoring endoprotheses spongiosa is totally removed from the bone and a remaining free space formed between the prothesis and compacta of the bone is filled with special fillers, for example bone cement. In this process used for conventional total protheses and for upper surface substituting endoprotheses and the combination of those depending on implantation technique, the thickness of the cement layer, elasticity coefficient and implantation time have been found inefficient (see, for example "Bony Ingrowth Fixation of Aeetabular Components for Canine Total Hip Replacement" by Harris, W.H., 27 Ann. Meeting Orth. Res. Soc. Vol. 6, page 74).

Tests and research have been conducted for ways of cement-free implantation possibilities which would suggest large volume prothesis shafts, longer prothesis shafts and better shaft-prothesis designs with smaller or thinner cement layers to be utilized.

This research, however, has practically failed because it is merely not possible to determine automatically when the prothesis with adjustable parts is to be used taking into consideration a real number of different lengths, widths of human joints and joint parts with use of filling and preliminarily prepared protheses.

The major problem with conventional techniques is also that eventually the endoprotheses become loosened after being inserted in place and must be readjusted. This happens with joints for total and joint surface substituting protheses and their combinations. With the upper surface substituting prothesis, important force receiving and force distributing bone structures (hard bone bark corticals) or bone mesh (spongiosa) must be removed, for example in cortical compact bone shaft tube for force receiving and force distribution and existing incongruities must be compensated by a filling material.

SUMMARY OF THE INVENTION

It is an object of the invention to provide a method of producing anatomically-shaped protheses or implants and the structures of such protheses which make individual anatonical shape of the prothesis possible. Only an individually anatomically shaped prothesis, particularly endoprothesis makes an optimal and reliable anchoring of the prothesis in the human bone and optimal biomechanic possible.

The endoprotheses of the invention can be individually adjusted to each concrete case of use so that an anatomical optimal seat in a bone for a prothesis or for anchoring the protehesis in the bone and a further maintenance of the structure of the bone carrying the prothesis are ensured. Thereby conditions for a continuous and effective anchoring of the prothesis are provided. The upper surface of the prothesis or the upper surface of the anchoring member can be provided with contemporary prothesis coatings which for example favorably affect the bone growth. The upper surfaces of the protheses can be smooth or porous rough layer in the direction of the upper surface growth, formed by grooves, laminations, prongs, openings, knubs, or the like. According to the invention, hollow prothesis-shaped members or meshed-network or plait-network protheses compatible with the spongiosa structure of the bone can be produced and protheses can be adjusted to the outer shape and structure of the bones. Various materials utilized in possible combinations, such as metal, plastics, ceramics, may be used.

With the protheses of the invention the utilization of bone cement is limited to minimum or its use is not required due to the fact that individual anatomic shapes and heights of protheses are obtained as a result of the method of the invention. Furthermore, individual biomechanical and therapeutic aspects can be more effectively taken in consideration in the method of the invention.

The invention can be used for individual forms and casts of other implants, for example for breast implants and others where initial moulding has been successfully used. Special plates, angular plates, screws, nails rods or the like elements utilized in surgery and orthopedics permit adjusting and producing of protheses according to individual structural conditions which include dimensions, a number and distribution of anchoring openings, the length of threads and the like. The important supporting plane of the plates or supporting collars of the protheses is precisely definable. Due to the defining of the anchoring area of the prothesis in the bone, such parameters as joint head diameter of the hip joint, shank collar length and various angular positions and articulated joint surface geometry of the other prothesis elements can be adjusted to the individual patients, for example to his or her body weight, pelvis or hip ratio, material friction ratio, lever arm ratio and size ratio.

The method according to the invention, due to the use of computers, significantly improves a safety factor. When a prothesis image is determined from the range of images a specialist can further define the contour shape of the prothesis also by deck pins or electronic pins or via covering of the cross-section course of the prothesis, however, the prothesis image received from the automatic scanning devices of the computer gives a clear contour of the prothesis.

The contour image received from the image range can be determined automatically by scanning, by means of light and electronic beams and storage of all examination data of each process step can be provided in the computer which automatically makes from the stored data a spatious combination of the range of the contour image and, in accordance with a given testing program, for example, collision measurement, makes necessary corrections and modifications in the contour image to adjust the same to the stored value. It is also possible, in the method according to the invention with a further application of the computer and spatious combination of the determined image range data, to transmit individually determined contour image ranges to a three-dimensional model by means of a copying receiver of a prothesis manufacturing machine.

The method of the invention can be applied to any material of the prothesis. In this connection, one of the last steps of the suggested method, namely the step of producing of the prothesis with the aid of the combination value is affected. Depending on the material utilized any material removing means can be suggested.

With metal or plastics materials the prothesis is produced by milling, polishing, turning, electrical erosion or pressing. All these processes should be performed taking into consideration the combination value received from the computer or according to a three-dimensional model preliminarily produced. The combination values can be also used for producing casting moulds for prostheses.

Individually formed prostheses according to the invention are adjusted in bones in their supporting regions. In case of a joint endoprothesis, such as a joint surface substituting element or a total joint substituting element, this individual adjustment is carried out in the region of the anchoring surface and in the region of the articulated joint surface. The whole geometry of caps, cords, muscles and fibers in the joint, and also the whole "bio-mechanics" are considered in the method. Important biomechanical and therapeutic aspects, such as axes positions, lengths, sizes and radii of joint parts are also considered. The method of the invention also permits the consideration of osteogenically efficient or also impact-dampening coating of the prothesis elements. Due to the application of computers it is possible to use a given control program for determining the spatious combination of adjusted image range data of individual images, and for determining a spatious combination of adjusted range data for a hollow space in the processes reliefs between the supporting regions, and the screw course upper surface of the prothesis anchoring element should be provided.

The particular advantages of application of computers resides in that the examination of load capacitance of each individually formed prothesis must not be an additional process step to be conducted on the prepared prothesis or prothesis mode but is performed by computer while determining the spacious combination of adjusted image range data with the aid of respective control programs (for example finite-element-program).

The prothesis may be produced from a blank by removing material therefrom to produce a contour according to a pattern received with the aid of the examined and modified stored combination value from the computer.

According to further features of the invention an endoprothesis which comprises an anchoring shaft to be inserted into a hole formed in a bone may be manufactured by the above-described method. The shaft may at least in the supporting regions thereof, in which it is supported in said hole, be formed with a plurality of individual circular steps, each of said steps having a contour individually adjusted to a respective cross-section of the hole, at which the respective step is located when the anchoring shaft is inserted into said hole.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DETAILED DESCRIPTION OF THE PREFERRED EMBODIMENT

Figures 1, 2, 3:
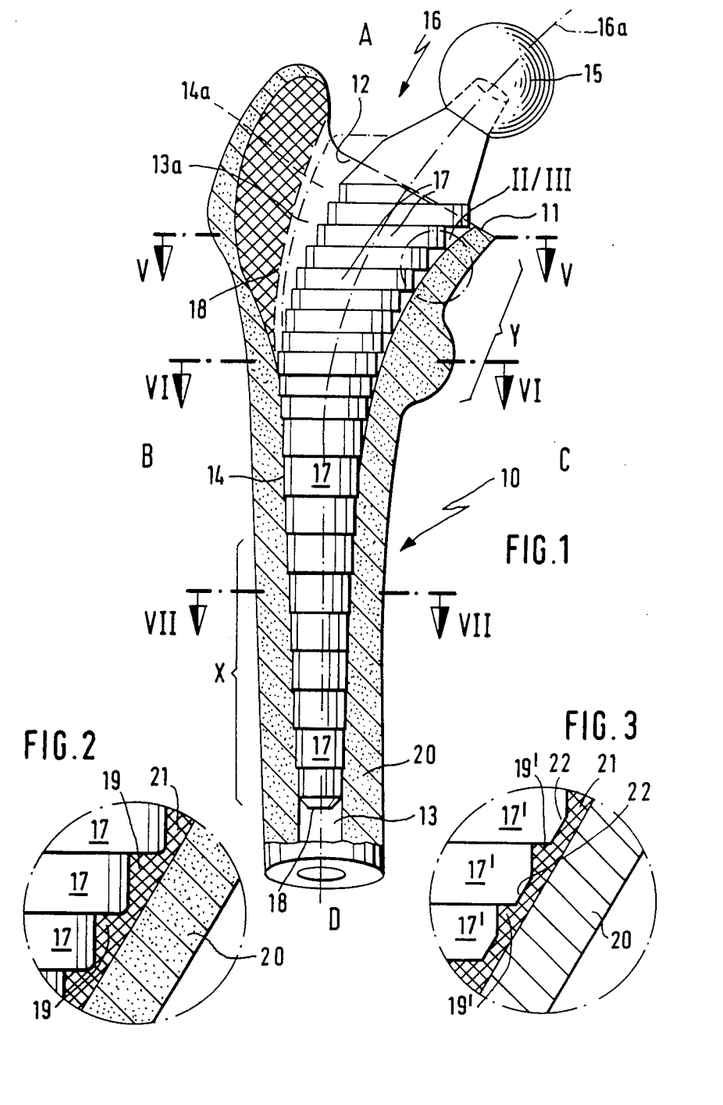
FIG. 1 is a longitudinal section through a so-called antetorsion plane of a hip joint endoprothesis.
FIG. 2 is a detailed view II of FIG. I, on the enlarged scale.
FIG. 3 is a detailed view II of FIG. 1, on the enlarged scale, according to a modified embodiment of the invention.
Figure 4:
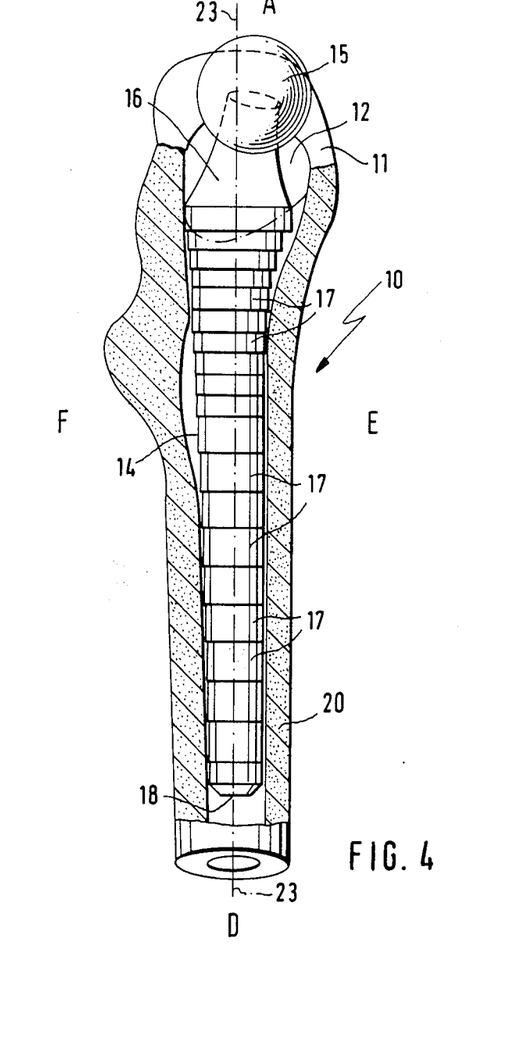
FIG. 4 is a longitudinal section of the bone with the endoprothesis of FIG. 1 but turned at 90° to the antetorsion plane.

Referring now to the drawings, FIGS. 1 and 4 show axial sectional views of the bone with the anchoring shaft inserted therein. Reference numeral 10 denotes an upper shank bone the sides of which are depicted in capital letters. Reference character A designates an upper side of the bone, D identifies a bottom side of the bone, B is an outer side, C is an inner side, E denotes a front side and F designates the rear side of the bone 10.

The head of the upper shank bone 10 is cut along plane 11. An opening 12 produced by scraping spongiosa from a bone hollow 13 extends from plane 11 to the bottom end of the bone. An anchoring shaft 14 of the joint head 15 of the hip joint endoprothesis is inserted into opening 12. The anchoring shaft 14 which extends along a partially curved axis 16a shown with dot-dashed line, is comprised of a number of individual adjacent steps 17. As seen in FIG. 1 steps 17 positioned along the straight portion of axis 16a and extended up to the end of the shaft have a relatively large height and are formed almost without laterally protruding portions or cuts. The width of successive steps 17 from the bottom end 18 upwardly varies so that the shaft is widened in a triangular mode. The steps forming the curved portion of the shaft curved at the shank neck and further widened also in triangular mode have a smaller height as compared to those extended downwardly towards the shaft end 18.

The contours of individual steps 17 are adjusted at least in the main supporting areas of shaft 14 identified by X and y to the cross section of bone hollow space 13 which receives the anchoring shaft 14. The adjustment of the contours of steps 17 in the bottom supporting area X is available over the whole periphery of the shaft. The adjustment of the contours of steps 17 to the surface defining space 13 in the upper supporting area Y is limited predominanty by the concave area of the anchoring shaft in the region of supporting area Y. In the convexly curved area opposite to area Y are steps 17 provided with undercuts and extended in the direction away from shaft end 18 the joint head 15; these steps are so arranged that due to efficient adjustability, they do not lie against the limiting wall defining the hollow space 13. After the insertion of the endoprothesis into space 13 the free zone 13a is filled with spongiosa; filling can be also obtained by filling a back area 14a behind the anchoring shaft.

FIGS. 2 and 3 illustrate steps 17 of shaft 14 in detail on the enlarged scale. Spaces 19 are located between the edges of individual steps 17. These spaces are, after the anchoring shaft has been inserted into the bone and clamped, filled with consolidated spongiosa so that a transition layer of spongiosa 21 remains in the supporting area Y, which layer lies on compacta 20 of the upper shank bone. FIG. 3 illustrates a portion of anchoring shaft 14 with steps 17 which are formed with crushed or straightened corners 22; this results in smaller spaces 19' between individual steps 17'.

In FIG. 4, line 23 defines the antetorsion plane.

Figure 5:
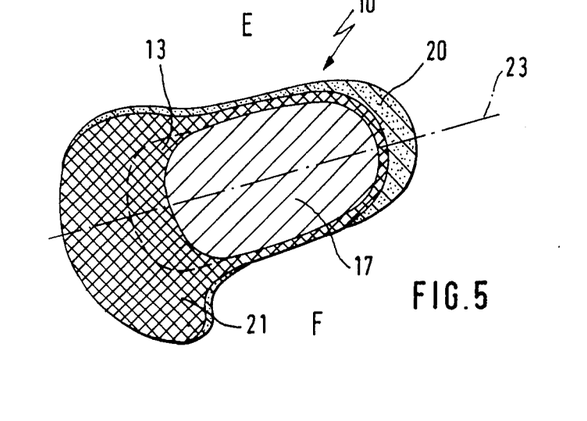
FIG. 5 is a sectional view on line V—V of FIG. 1.
Figure 6:
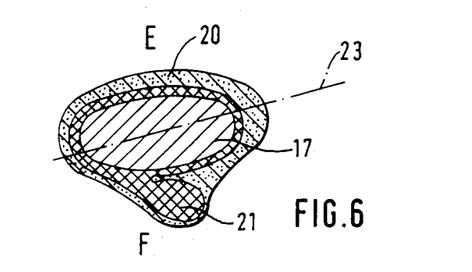
FIG. 6 is a sectional view on line VI—VI of FIG. 1.
Figure 7:
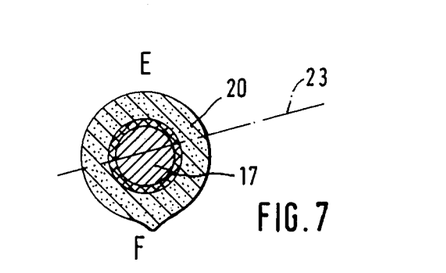
FIG. 7 is a sectional view on line VII—VII of FIG. 1.
Figure 8:
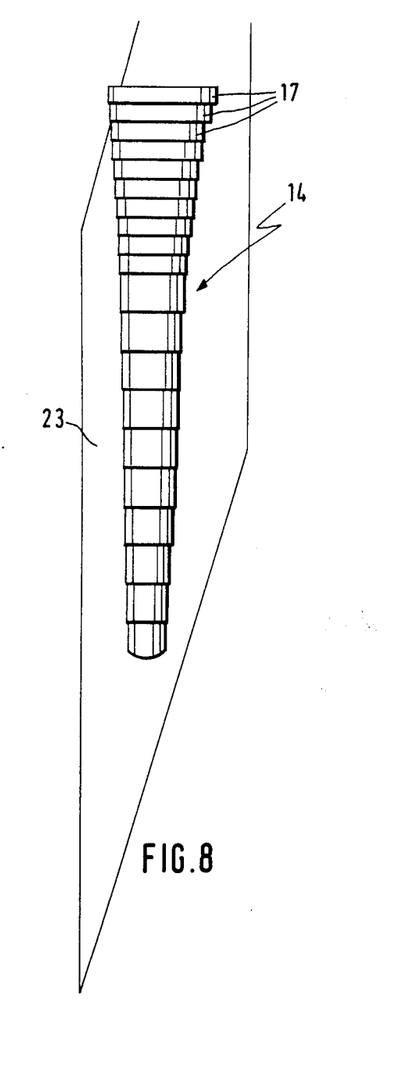
FIG. 8 shows an anchoring shaft of the hip joint endoprothesis in the antetorsion plane.
Figure 9:
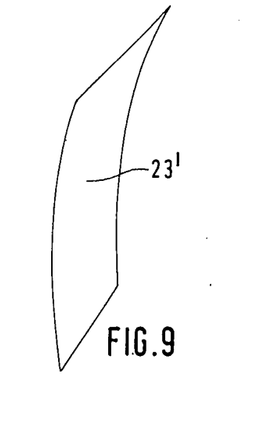
FIG. 9 shows a curved antetorsion plane.
Figure 10:
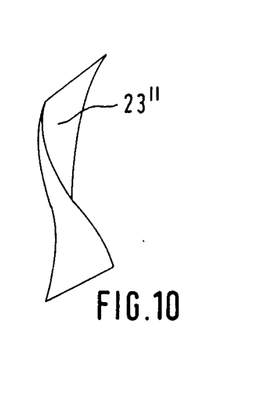
FIG. 10 shows a twisted antetorsion plane.

Cross-sections shown in FIGS. 5, 6 and 7 and taken through the bone 10 of FIG. 1 illustrate an adjustment of various contours of individual sections of steps 17 of the anchoring shaft to the contours of bone hollow space made by scraping of spongiosa from the bone. The spongiosa layer areas 21 are shown in sectional views of FIGS. 5-7 by cross-hatching and are distinguished from compacta areas 20 of the upper shank bone. Line 23 in FIGS. 5-7 denotes a course of the antetorsion plane which is selected in accordance with antetorsion angle of the upper shank-joint head and with which is anchoring shaft 14 aligned. The curved antetorsion plane also possible with the anchoring shaft 14 is schematically shown in FIG. 9. The view of FIG. 8 corresponds to the section of FIG. 4 lane 23 in FIG. 8, is a straight antetorsion plane FIG. 10 schematically shows antetorsion plane 23 which is not only curved but also twisted; the anchoring elements of the hip joint endoprothesis can be formed in accordance with plane 23".

Figure 11:
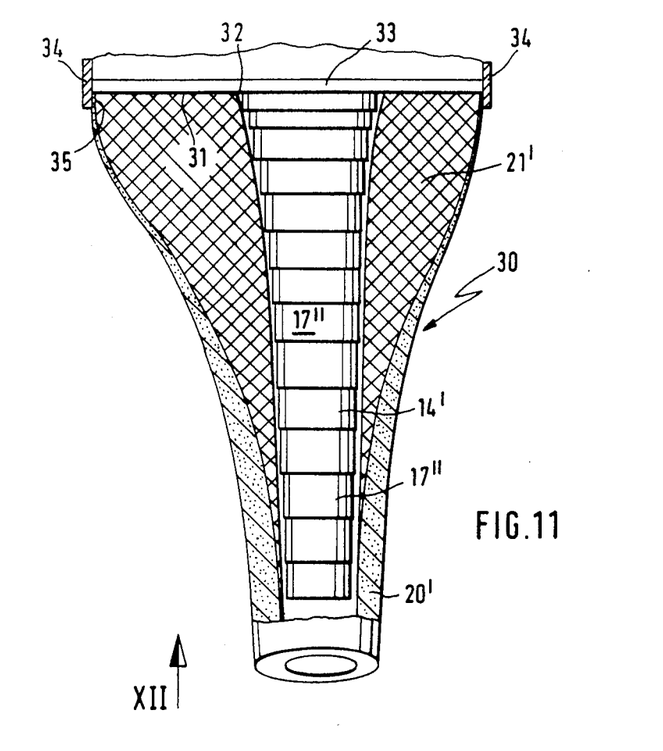
FIG. 11 is a sectional view of the shin bone with the endoprothesis inserted therein.
Figure 12:
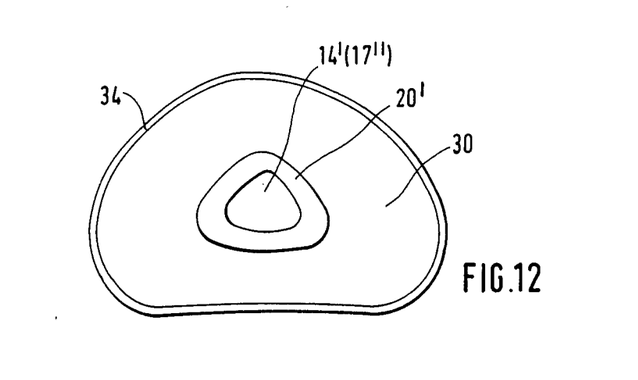
FIG. 12 is a view from below of the shin bone of FIG. 11.

FIG. 11 illustrates anchoring shaft 14' which is straight and formed with a plurality of superimposed steps 17", which is a portion of a knee joint endoprothesis which is anchored in a shin bone 30. The head of the shin bone 30 only partially seen in the drawing is separated from the lower part thereof by a surface 31. There also is formed a bone hollow space 32 from a spongiosa 21' for receiving shaft 14' which is triangularly widened in the direction towards the head of the shin bone. In the narrowed region of the shaft are steps 17" arranged which are individually adjusted with their contours to the corresponding cross-sections of the hollow space 32. At the end portion of shaft 14' steps 17' lie directly against compacta 20'as seen in FIG. 12. A plate 33 is positioned on the upper end of anchoring shaft 14' which plate covers the whole surface 31 of the shin bone 30. Plate 33 also has a rim or flange 34 which corresponds to the outer edge of surface 31 of the bone and surrounds with its lower portion an edge 35 of the bone. Plate 33 with its flange 34 forms a lock of endoprothesis with its stepped anchoring shaft 14' against rotation.

Figure 13:
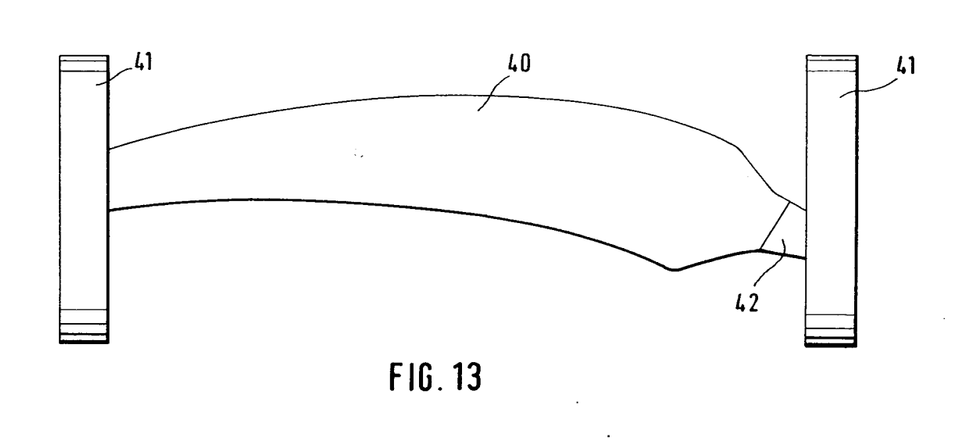
FIG. 13 is a side view of a blank for producing an endoprothesis shown in FIGS. 1-4.

FIG. 13 shows a blank 40 for endoprothesis forged for example of steel alloy. Disc elements 41 parallel to each other are connected to the blank at both sides of prothesis blank 40 for example by welding, for holding and centering it in the machine provided with a material removing tool. Blank 40 is used for manufacturing a hip joint prothesis 16 with the stepped anchoring shaft shown in FIG. 1. After the stepped shaft has been produced elements 41 are removed therefrom.

Shaft 14 is manufactured from blank 40 according to a pattern received from the computer as described wherein above.

A detecting of the image range in the individually defined images of bones or other body parts can be obtained by means of rasters used in software of the computers so as to define important contour points for determining the periphery of the endoprothesis. This raster can be, for example a grid raster covering an individual range image.

Figure 14:
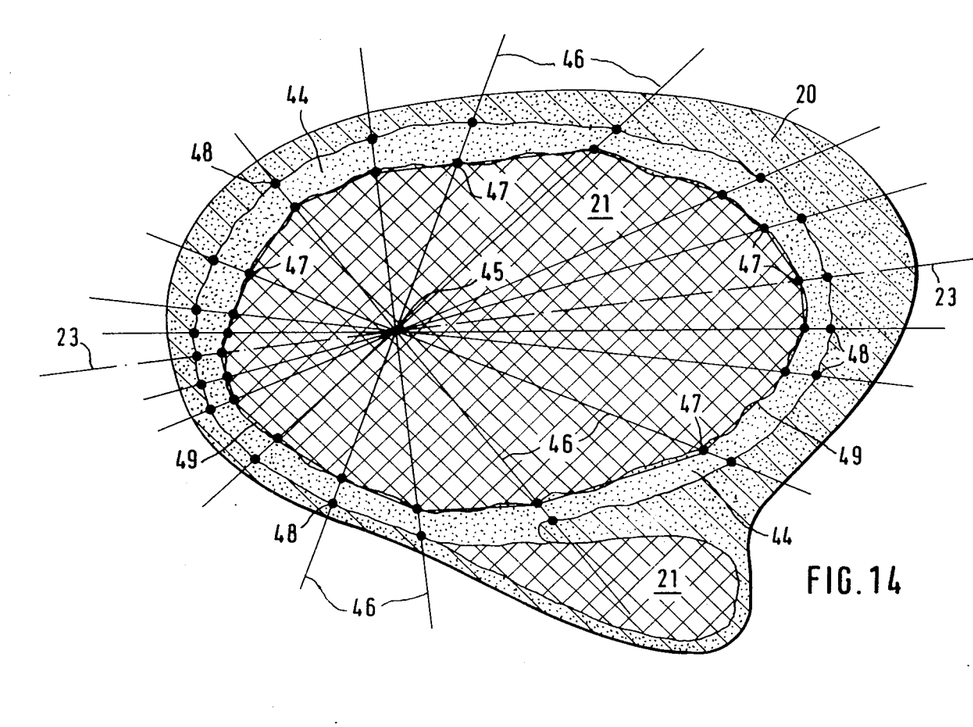
FIG. 14. is a sectional view corresponding to that of FIG. 6; through the bone, with an evaluation raster.

FIG. 14, which substantially corresponds to FIG. 6, shows an asterisk raster which is originated from point 45 lying in antetorsion plane 23. This point 45 can also extend through axis 16a shown in FIG. 1. This axis on which points 45 of successive range images lie can be curved or twisted. Asterisk lines 46 of the raster are detected due to the changes in thicknesses between compacta 20 and spongiosa 21, or by detecting the beginning point 46 of the transition zone between compacta 20 and spongiosa 21 or beginning point 48 (if greater thickness changes take place). Revised contour values, for example straight or angular, would be automatically received from points 47 and 48 and contour 49 of the endoprothesis 16(17) will be obtained from those corrected values, to be used for producing the endoprothesis.

It will be understood that each of the elements described above, or two or more together, may also find a useful application in other types of methods of producing individually formed differing from the types described above.

While the invention has been illustrated and described as embodied in a method of producing individually shaped protheses and implants, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An endoprothesis comprising an elongated shaft dimensioned to be anchored through a bone opening in a bone cavity, said shaft being formed in one piece having a shape composed by a plurality of individual disc-like segments of different shapes forming a tapered stepped profile without undercuts from a proximal end to a distal end of said shaft; said shapes of said individual disc-like segments having outer perimeters adjusted to substantially match the corresponding cross sections of the bone cavity in order said implanted shaft to be fitted snugly to the bone cavity at least in regions of said shaft in which a support of said implanted shaft to the bone takes place when said endoprothesis is loaded.

2. The endoprothesis as defined in claim 1, wherein surfaces which limit adjacent disc-like segments of said shaft include an angle of 90° with each other.

3. A endoprothesis as defined in claim 1, said shaft defining a longitudinal axis therethrough and having a curved proximal portion, a straight distal portioln and a joint ball head at its proximal end, said joint ball head being positioned outside of a main axis of said shaft, said main axis being the longitudinal axis of said straight distal portion; said longitudinal axis of said shaft being aligned with an antetorsion plane of said shaft which is defined by maximum diameters of all said individual disc-like segments of said shaft.

4. The endoprothesis as defined in claim 3, wherein said antetorsion plane is curved.

5. The endoprothesis as defined in claim 3, wherein said antetorsion plane is twisted.

6. The endoprothesis as defined in claim 1, wherein said disc-like segments of said shaft have edges with cut-off corners.

7. The endoprothesis as defined in claim 1, wherein the heights of said disc-like segments of said shaft are different.

8. The endoprothesis as defined in claim 1, further including a covering plate mounted at the proximal end of the shaft and closing a bone surface and said bone opening, said covering plate being formed with a flange surrounding an edge of the bone surface.

* * * * *